United States Patent [19]

Pokora et al.

[11] Patent Number: 4,992,372

[45] Date of Patent: Feb. 12, 1991

[54] METHOD FOR REMOVING IMPURITIES FROM PEROXIDASE SOLUTIONS

[76] Inventors: Alexander R. Pokora; Mary M. Stanley; William L. Cyrus, Jr., all of The Mead Corporation, Mead World Headquarters, Courthouse Plaza Northeast, Dayton, Ohio 45463

[21] Appl. No.: 305,311

[22] Filed: Feb. 2, 1989

[51] Int. Cl.$^5$ .............................................. C12N 9/08
[52] U.S. Cl. ................................. 435/192; 435/814; 435/816
[58] Field of Search ............... 435/192, 814, 816, 800, 435/815

[56] References Cited

U.S. PATENT DOCUMENTS

| | | | |
|---|---|---|---|
| 2,703,779 | 3/1955 | Lolli et al. | 435/192 |
| 3,947,324 | 3/1976 | Lakshminarayanan | 435/192 |
| 4,135,980 | 1/1979 | Ikuta et al. | 435/191 |
| 4,194,067 | 3/1980 | Keyes | 435/192 |
| 4,228,240 | 10/1980 | Dawson et al. | 435/192 |
| 4,328,312 | 5/1982 | Tsurumi et al. | 435/192 |
| 4,331,761 | 5/1982 | Dawson et al. | 435/192 |
| 4,451,569 | 5/1984 | Kobayashi et al. | 435/188 |
| 4,647,952 | 3/1957 | Pokora et al. | 503/225 |
| 4,657,864 | 4/1987 | Lo | 435/192 |
| 4,698,306 | 10/1987 | Noda et al. | 435/192 |
| 4,707,447 | 11/1987 | Hunter et al. | 435/192 |
| 4,724,203 | 2/1988 | Sharma | 435/192 |
| 4,764,468 | 8/1988 | Wehner et al. | 435/192 |

*Primary Examiner*—Herbert J. Lilling

[57] ABSTRACT

A method for purifying an aqueous peroxidase enzyme containing solution and peroxidase solution purified thereby are disclosed; the method includes the steps of:
- providing an aqueous solution containing a peroxidase enzyme;
- adding a water-immiscible or partially water-miscible organic solvent to said aqueous solution to form a mixture having an organic phase and an aqueous phase;
- agitating said mixture to extract impurities from said aqueous phase into said organic phase;
- separating said aqueous phase from said organic phase; and
- discarding said organic phase.

8 Claims, No Drawings

METHOD FOR REMOVING IMPURITIES FROM PEROXIDASE SOLUTIONS

BACKGROUND OF THE INVENTION

1. Field of the Invention

The present invention relates generally to the purification of peroxidase enzymes, and more particularly, to a method for removing impurities from an aqueous solution containing horseradish peroxidase by using extraction techniques.

2. Description of the Prior Art

Peroxidase enzymes are fairly ubiquitous, occurring in higher plants, yeasts, molds, bacteria and mammals. One of the most common peroxidase enzymes is horseradish peroxidase. Horseradish peroxidase is produced from aqueous extracts of diced or ground-up whole horseradish roots, horseradish skin extracts or washings, or washings of whole horseradish.

Horseradish peroxidase has many uses. One such use is as an agent employed in immunossays. Another use of horseradish peroxidase is in the formulation of biocides. In an associated use, the horseradish peroxidase enzyme is particularly suited for its ability to catalyze the oxidation of phenolic materials (see, for example, U.S. Pat. Nos. 4,370,199; 4,478,683; and 4,647,952). As is known in the art, the oxidation of phenol typically occurs by utilizing a peroxide-peroxidase enzyme system, and more particularly, a hydrogen peroxide/horseradish peroxidase enzyme system.

Although horseradish peroxidase enzymes have been successfully used for the above applications, they are limited in their efficacy as a result of contamination. Microbial and lipophilic contamination appears to be the major contributing factor for the instability of peroxidase enzymes. Further, protease enzymes, a class of enzymes which hydrolyze proteins to amino acids and polypeptides, are water soluble products which degrade proteins and can degrade peroxidase. This too reduces the efficacy of utilizing horseradish peroxidase.

Alternatives have been proposed for purifying peroxidase enzymes. For example, U.S. Pat. No. 3,947,324 assigned to G. D. Searle discloses a method for isolating peroxidase enzyme from plant tissue containing peroxidase. The method includes treating aqueous extracts of plant tissue having a pH adjusted to 6-9 with an amount of zinc ion to form a zinc ion-protein contaminant precipitate and a supernate, removing the precipitate, and separating the peroxidase enzyme from the supernate. The reference further discloses that the separating step comprises absorbing the concentrated supernate on carboxymethyl cellulose, eluting peroxidase from the carboxymethyl cellulose with an aqueous buffer, precipitating the peroxidase from the aqueous buffer with an organic solvent, and filtering and drying the precipitate.

U.S. Pat. No. 4,657,864 assigned to Westvaco discloses a method for stabilizing peroxidase solutions. The method described in the reference comprises selecting a peroxidase solution of low protease content or treating the peroxidase solution to reduce its protease content, and then filtering the solution through a microporous membrane to sterilize and remove from the solution any microbial contamination that might secrete additional protease enzyme. According to the reference, the filtration membrane has a pore size ranging from about 0.20 to about 0.45 microns.

U.S. Pat. No. 4,043,870 assigned to Upjohn discloses a process for purifying aqueous solutions which contain cholestrol oxidase. In particular, the reference discloses a process for removing non-ionic surfactants from a solution containing cholestrol oxidase by extraction with a water-immiscible solvent and precipitation of the oxidase with a salt. According to the reference, the preferred solvent used is n-butanol and suitable salts for precipitation of cholestrol oxidase include ammonium sulfate, magnesium sulfate, sodium sulfate, potassium sulfate and the like.

Although the above described methods may be used to purify peroxidase enzymes, they are not ideally suited for all applications in that they are either costly, or require the addition of reactive materials which precipitates out either the peroxidase enzyme or the contaminant. Accordingly, there exists a need for a simple and cost efficient method for removing impurities from solutions containing peroxidase enzymes.

SUMMARY OF THE INVENTION

In accordance with present invention, a simple, cost efficient method for removing impurities, particularly lipophilic impurities, from aqueous solutions containing peroxidase enzymes is provided. The method is characterized by utilizing a simple extraction procedure involving an organic solvent so that the impurities contained in the aqueous peroxidase solution are extracted into the organic solvent.

In accordance with one embodiment of the present invention, a process for removing impurities from an aqueous peroxidase solution is provided. The process includes the steps of providing an aqueous solution containing peroxidase; adding a water-immiscible or partially water-miscible organic solvent to the aqueous solution to form a mixture having an organic phase and an aqueous phase; agitating the mixture to extract impurities from the aqueous phase into the organic phase; separating said aqueous phase from said organic phase; and discarding the organic phase.

In practice, the preferred organic solvent for use in the extraction procedure is ethyl acetate, the extraction takes place at room temperature, and at a pH between about 5 and about 8.

Another embodiment in the present invention provides a purified peroxidase enzyme solution wherein the purification is conducted by using the above-described process. Purified solution may be used for a number of practical applications, including use in the oxidative coupling reactions of phenolic materials.

DETAILED DESCRIPTION OF THE PREFERRED EMBODIMENTS

While describing the preferred embodiments, specific terminology will be utilized for the sake of clarity. It is to be understood that such terminology includes not only the recited embodiments, but all technical equivalents which performs substantially the same function in substantially the same way to obtain the same result.

While the inventive process is useful in purifying peroxidase enzymes generally, it is particularly designed to remove impurities from aqueous solutions containing horseradish peroxidase. Such solutions are commercially available An example of one such solution is Finnsugar Peroxidase IG. These solutions typically comprise horseradish peroxidase powder dissolved in deionized water. The solutions may also contain a pH buffer such as potassium phosphate.

To remove lipophilic or other microbial impurities from the peroxidase solution, a water-immiscible or partially water-miscible solvent is added to the aqueous solution. The solvent acts to extract the impurities from the aqueous solution and into the organic solvent. More particularly, the organic solvent should be capable of dissolving the impurities without dissolving the horseradish peroxidase to ensure maximum recovery of the peroxidase enzyme.

The solvent may be selected from amongst a number of known solvents used for extraction processes. Examples include n-hexane, ethyl acetate, dichloroethane and methyl isobutylketone.

In practice, it is preferable to add between about 30 parts to about 500 parts of organic solvent per 50 parts aqueous solution. It is particularly preferred to add approximately 200 parts solvent per 50 parts of aqueous solution.

After addition of the organic solvent, a two liquid mixture results containing an aqueous phase including the horseradish peroxidase enzyme and an organic phase consisting primarily of the organic solvent. The mixture is then agitated to enable the contents of each of the liquid phases to come into contact. The agitation causes the lipophilic and other microbial impurities to be extracted from the aqueous phase to the organic phase. When the impurities are soluble in the organic solvent, they are dissolved into the organic phase upon agitation.

The agitation step is preferably carried out at temperatures between about 5° C. and about 40° C. It is particularly preferred that the temperature be maintained between about 20° C. and about 30° C. If the agitation step takes place at higher temperatures, i.e. greater than 60° C., the catalytic properties of horseradish peroxidase are rendered ineffectual. Accordingly, it should be ensured that agitation not take place at elevated temperatures.

In addition, it is preferred that the pH of the aqueous solution be maintained between about 4 and about 12, more preferably, between 5 and 8. Buffers can be used to maintain pH, but are not required. One example of a useful buffer is a potassium phosphate buffer.

The agitating may be accomplished by any of the means known in the art. For example, agitation may be accomplished by shaking, stirring, blending, and the like. In practice, it is particularly preferred to use a stirrer operating at a rate of between about 50 and about 500 revolutions per minute.

In addition to the agitating step, means should be utilized to facilitate phase separation of the aqueous phase from the organic phase. This is preferably accomplished by centrifuging the mixture for a period of time sufficient to enable the different specific gravity phases to effectively separate. In practice, a centrifugation time ranging between about 1 minute and about 20 minutes is selected.

Once the agitation step has been completed, the organic phase containing the impurities is discarded, leaving a aqueous phase containing purified horseradish peroxidase. In practice, the purified aqueous solution may be used for practical applications or, if desired, the horseradish peroxidase may be isolated from the remainder of the aqueous phase by procedures known in the art such as microfiltration.

One particular application for the produced purified horseradish peroxidase solution is its use in the polymerization of phenolic resins. This use is described in greater detail in U.S. Pat. No. 4,647,952, which is hereby incorporated by reference. According to the teachings of this patent, a phenol material is polymerized by free radical coupling ARP polymerization using a peroxideperoxidase enzyme system as an initiator material The preferred peroxide used is hydrogen peroxide and the preferred peroxidase enzyme is horseradish peroxidase. It has been discovered that by using the purified horseradish peroxidase solution of the present invention as part of the initiator system, a better polymer in terms of purity and appearance is produced.

Other peroxidases purifiable by the present invention are disclosed in U.S. Pat. No. 4,647,952.

The invention is illustrated in more detail by the following, non-limiting examples.

EXAMPLE 1

100 parts of ethyl acetate were added to 100 parts of a Finnsugar Peroxidase IG crude horseradish peroxidase aqueous solution at 20° C. The resulting mixture was stirred at 100 rpm for 10 minutes. Subsequently, the mixture was centrifuged at 2,700 rpm for 10 minutes. After centrifuging, the organic layer was discarded, leaving a purified aqueous phase.

COMPARATIVE EXAMPLE 2

12.3 ml of Finnsugar Peroxidase IG crude horseradish peroxidase solution dissolved in 200 ml of deionized water and 100 grams of Bisphenol A dissolved in 140 ml of methanol and 60 ml of ethyl acetate were added to a three-necked 1000 ml round bottom flask. 100 ml of 15% hydrogen peroxide solution was added dropwise over a four hour period while stirring constantly. The reaction was allowed to proceed for ten minutes after the addition of the reagents. The product was collected by filtration and examined under a microscope. The produced resin contained an amount of dark particulate material.

EXAMPLE 2

The experiment of Comparative Example 2 was repeated with the exception that instead of using 12.3 ml of the crude horseradish peroxidase solution, 24.6 ml of the reaction product of Example 1 dissolved in 188 ml of deionized water was used. The produced resin was clear and colorless and did not possess any particulate material.

Having described the invention in detail and by reference to preferred embodiment thereof, it will be apparent that modifications and variations are possible without departing from the scope of the invention defined in the appended claims.

What is claimed is:

1. A process for removing impurities from an aqueous peroxidase enzyme containing solution comprising the steps of:

providing an aqueous solution containing a peroxidase enzyme;

adding a water-immiscible or partially watermiscible organic solvent to said aqueous solution to form a mixture having an organic phase and an aqueous phase;

agitating said mixture to extract impurities from said aqueous phase into said organic phase;

separating said aqueous phase from said organic phase;

discarding said organic phase and recovering said enzyme from said aqueous phase.

2. The process of claim 1 wherein said peroxidase enzyme is horseradish peroxidase.

3. The process according to claim 2 wherein the amount of said solvent added to said aqueous solution is approximately 30 to 500 parts per 50 parts of said aqueous solution.

4. The process according to claim 2 wherein said solvent is selected from the group consisting of n-hexane, ethyl acetate, methylisobutylketone and dichloroethane.

5. The process according to claim 4 wherein said adding and agitating steps are performed at a temperature between about 5° C. and about 40° C.

6. The process according to claim 4 wherein said mixture is maintained at a pH ranging from about 4 to about 12.

7. The process according to claim 4 wherein said agitating step comprise stirring said mixture.

8. The process according to claim 7 wherein said separating step comprises centrifuging said agitated mixture.

* * * * *